US007150722B1

(12) United States Patent
Tyrrell

(10) Patent No.: US 7,150,722 B1
(45) Date of Patent: Dec. 19, 2006

(54) THERAPEUTIC WALKER

(76) Inventor: Anthony Tyrrell, 5229 NW. 108th Ave., Sunrise, FL (US) 33351

( * ) Notice: Subject to any disclaimer, the term of this patent is extended or adjusted under 35 U.S.C. 154(b) by 0 days.

(21) Appl. No.: 11/139,281

(22) Filed: May 27, 2005

(51) Int. Cl.
*A61F 5/00* (2006.01)

(52) U.S. Cl. .......................................... 602/23; 602/26

(58) Field of Classification Search .................. 602/23, 602/26, 5, 20, 28, 29, 60; 128/870, 871, 128/869; 482/51, 88, 124, 39, 42, 134; 135/65, 135/75, 85, 88.01, 88.06
See application file for complete search history.

(56) References Cited

U.S. PATENT DOCUMENTS 4,960,115 A * 10/1990 Ranciato ...................... 602/23
5,467,793 A 11/1995 Hart
5,588,456 A 12/1996 Hart
5,732,964 A 3/1998 Durham
5,795,269 A 8/1998 Bawtree
6,607,202 B1 8/2003 Palmer
6,832,770 B1 12/2004 Wrigh-Ott

* cited by examiner

*Primary Examiner*—Justine R. Yu
*Assistant Examiner*—Shumaya B. Ali
(74) *Attorney, Agent, or Firm*—Alvin S. Blum

(57) ABSTRACT

A walking support apparatus for a person wearing a body brace has a rigid wheeled frame. An upright support engages a torso-encircling brace member. A chest-engaging member is mounted on the support. A person is connected to the apparatus while on a seat removable attached to the frame. The person is then lifted to a standing position by cranking up the support. A mechanism mounted behind the support anchors first ends of two cords that connect at second ends to the knees. It prevents both knees from moving forward simultaneously. One knee moves forward while taking up slack in the other cord. Shoe cords enable moving one foot forward at a time, and prevent both feet moving backward together. Elastic elements in shoe cords provide assistance at beginning of stride.

16 Claims, 4 Drawing Sheets

THERAPEUTIC WALKER

This invention relates to walking apparatus and supports, and more particularly to apparatus to facilitate walking by a disabled person.

BACKGROUND OF THE INVENTION

Persons with disabilities such as cerebral palsy are often provided with braces and walkers such as those described in U.S. Pat. No. 6,607,202 issued Aug. 19, 2003 to Palmer and U.S. Pat. Nos. 5,588,456 and 5,467,793 issued to Hart to enable the person to walk. The walkers of the prior art do not provide the user with a gait close to that of a normal person. Consequently, they do not properly exercise the body muscles.

SUMMARY OF THE INVENTION

It is accordingly an object of the invention to provide walker apparatus that will encourage a more normal gait to develop the body muscles in a more normal manner.

In a first embodiment of the invention, a rigid frame is provided with front and rear wheels. The user stands between the front and rear wheels. Individual knee connections at the knee connect by cords to the rear of the frame. The knee connections may be cuffs to the patient or to leg braces at or near the knee. Individual shoe cords connect from the front of the frame to the shoes of the patient or to braces at the shoes. The knee connections are connected to the walker by individual cords with a special mechanism. The mechanism enables a forward moving knee to move forward in the walker during its stride. The mechanism takes up slack in the cord to the stationary knee without pulling on it. This more closely relates to the normal walking gait than the prior art apparatus. The mechanism prevents both knees from moving forward together.

The shoe cords enable the patient to move one foot forward at a time. They may include an elastic element to bias the rear shoe forward at the end of a stride. This provides spring bias to assist the rear foot in moving forward at the beginning of its stride. The shoe cords prevent both feet from moving backward together.

An embodiment of the apparatus of the invention comprises a torso encircling body brace with leg braces having articulations at the hips and knees and ankles. The wheeled frame includes a vertical support with adjustable connection for engaging the back of the body brace as well as a vertically adjustable chest holder. The body brace may be mounted on the patient away from the walker. The walker may be provided with a removable seat, so that the patient may be fitted with a body brace and may then be comfortably seated on the walker. The seated patient may then be connected to the walker. The connections to the walker include: the chest holder; the back of the body brace; individual below-the-knee cuffs that connect from rear of the frame to the patient; and individual shoe cords that connect the front of the frame to the patient. A vertical support member extends upward from the frame. The chest holder is connected to the vertical support member. A connection on the vertical support member below the chest holder removably engages the back of the body brace. The chest connection to the vertical support member and/or the back of the body brace connection to the vertical support member may be vertically adjustable so that the distance between the chest holder and the brace holder may be adjusted to the size of the patient.

The shoe cords may be provided with an elastic portion that actuates at the end of a stride to assist in the next step. These connections to the body brace may be made while the patient is seated. The vertical support member is provided with a vertical adjustment so that the patient may be connected to the waker while seated, and then lifted to a standing position by the vertical support member adjustment mechanism.

These and other objects, features, and advantages of the invention will become more apparent when the detailed description is studied in conjunction with the drawings in which like elements are designated by like reference characters in the various drawing figures.

DETAILED DESCRIPTION OF PREFERRED EMBODIMENTS

Figure 4:
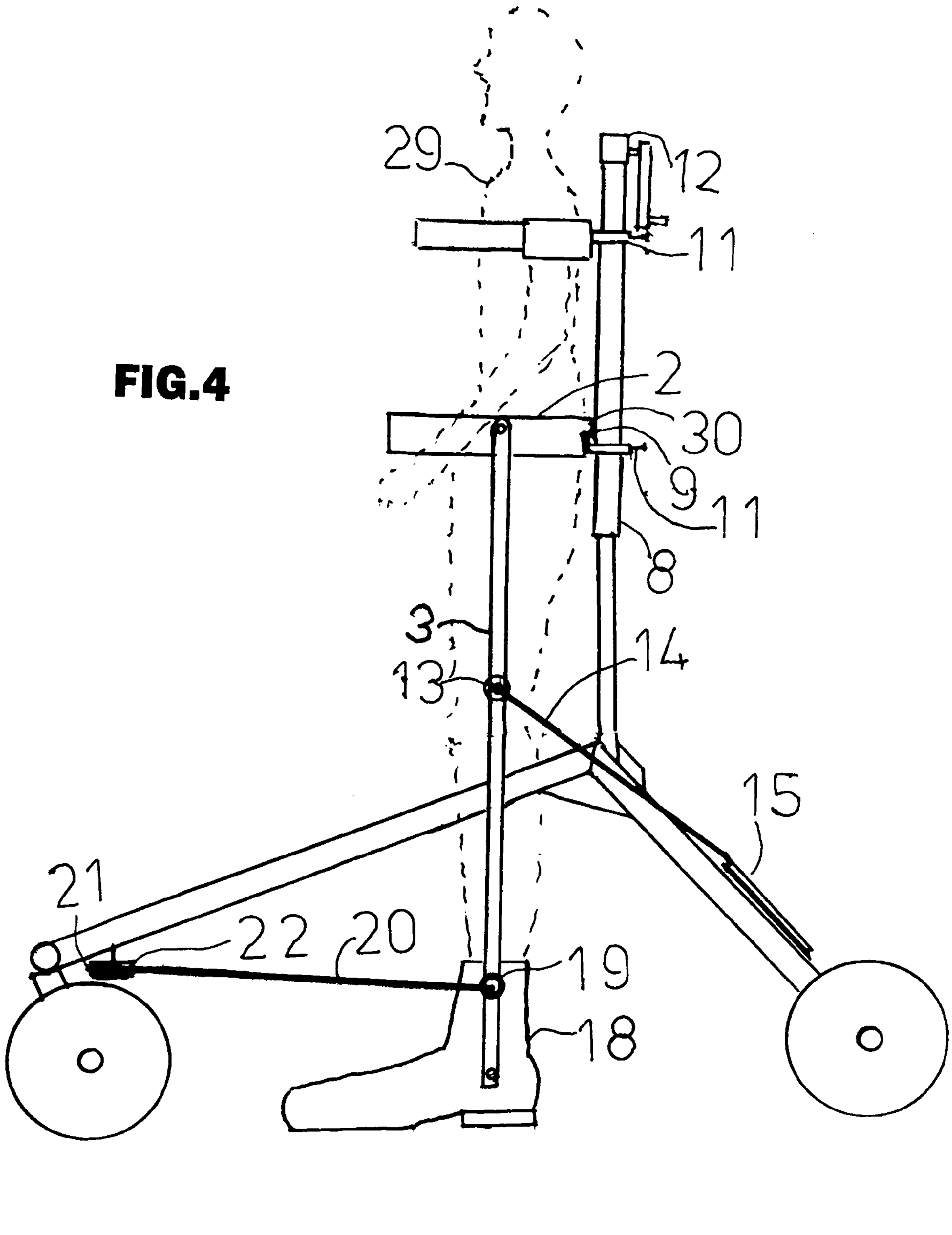
FIG. 4 is a side elevation view of the walker of the invention with a standing patient shown in phantom.

Referring now to the drawing figures, a rigid frame 1 has a pair of front castor wheels 5 and a pair of rear wheels 6. Although the frame may be supported by three wheels, four are preferred for stability. A seat 7 may be removably mounted on the frame above the level of the wheels, so that the person may be more easily connected to the frame while seated. As best seen in FIG. 4, the person 29 is generally fitted with a brace comprising a torso-encircling member 2 and articulated leg braces 3 depending therefrom with shoes 18 pivotally attached at the ends of the leg braces. A vertical support member 8 extends upward from the frame behind the seat and forward of the rear wheels. Engagement means 9 mounted on the vertical member 8 is adapted to engage the rear portion 30 of the torso-encircling member 2. A chest engaging member 10 may be strapped about the chest to keep the person upright. Vertical adjustment mechanisms 11 enable the members 9 and 10 to be adjusted on the vertical member 8 to fit a particular person. The person and vertical member 8 may be elevated by crank mechanism 12 to raise the seated person to a standing and walking position after the brace and chest engaging member have connected the person to the vertical support member. Then the seat may be removed. This is especially useful in working with a heavy or uncooperative patient.

Figure 5:
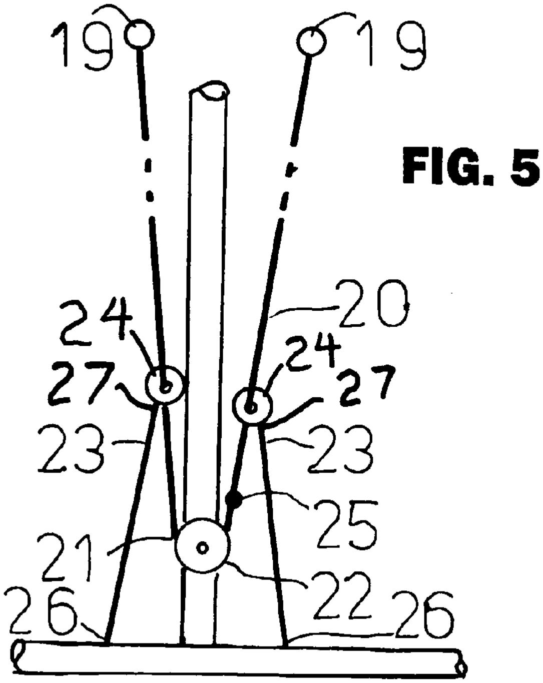
FIG. 5 is a detail view of the shoe control mechanism of the invention.
Figure 1:
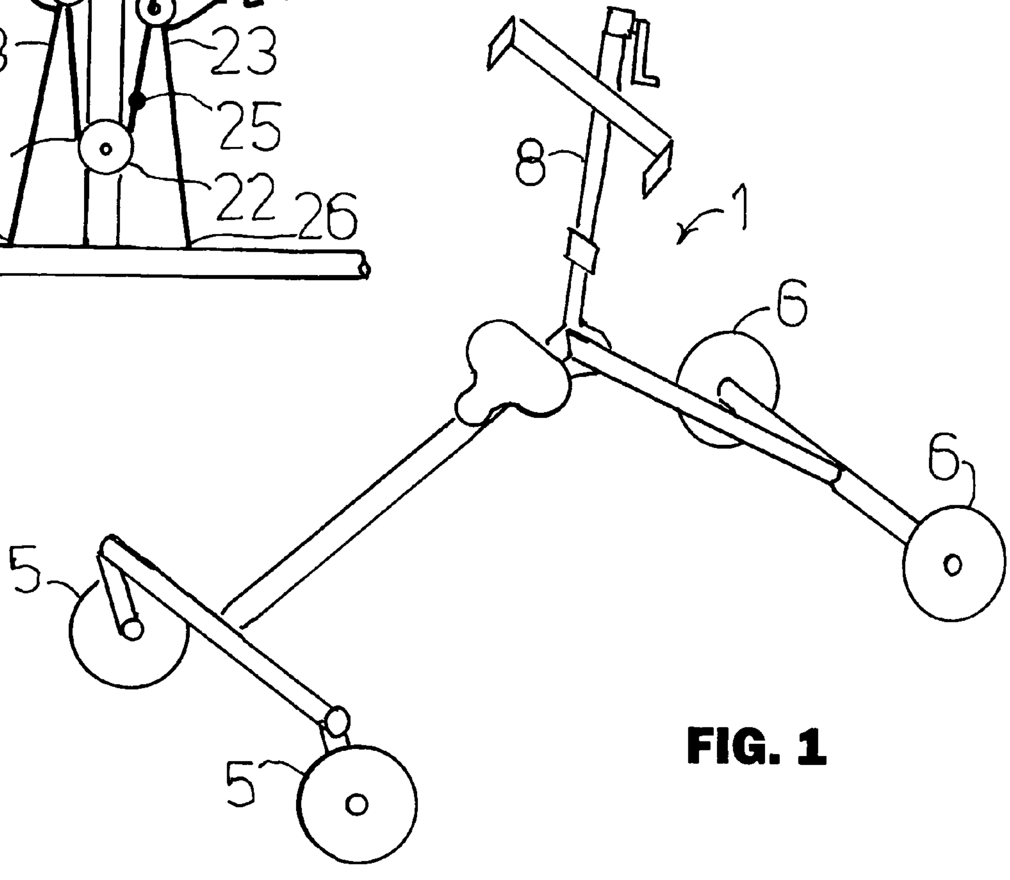
FIG. 1 is a perspective view of the frame of the invention.
Figure 7:
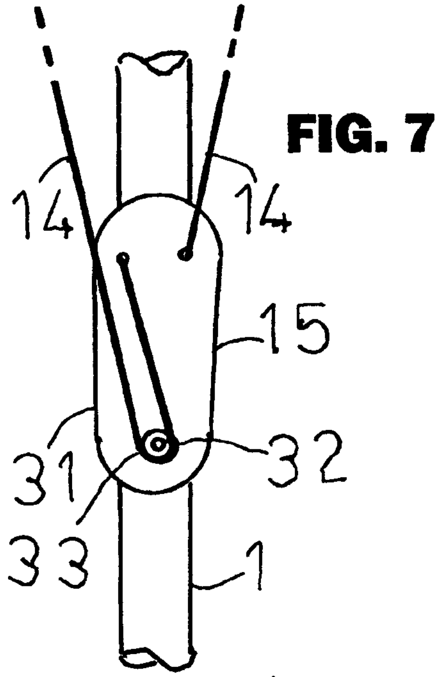
FIG. 7 is a detail view of the knee control mechanism of the invention when patient has moved the right knee forward.
Figure 6:
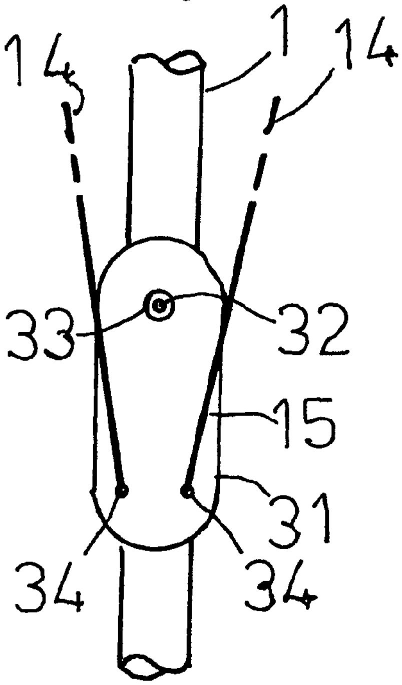
FIG. 6 is a detail view of the knee control mechanism of the invention when patient is standing.
Figure 2:
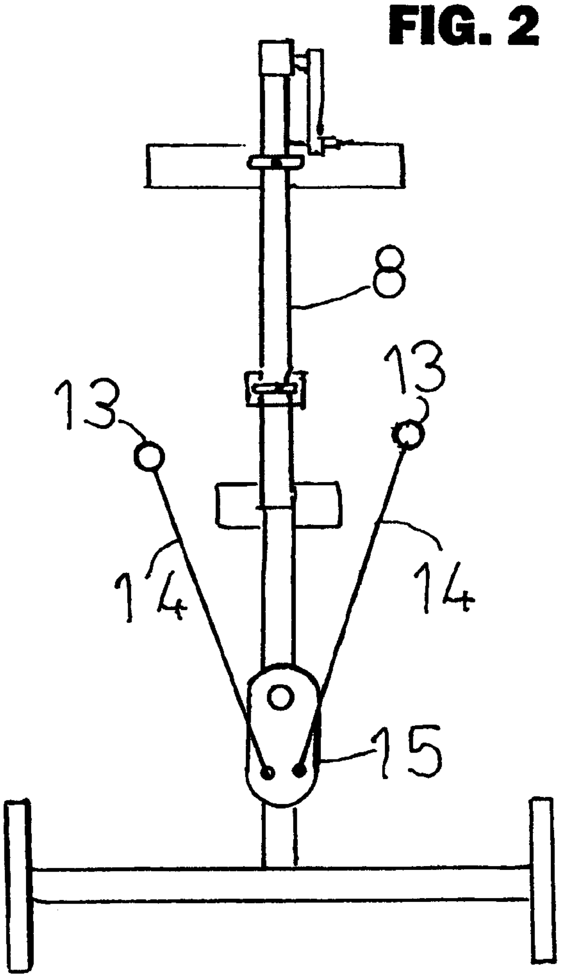
FIG. 2 is a rear elevation view of the walker of the invention.
Figure 3:
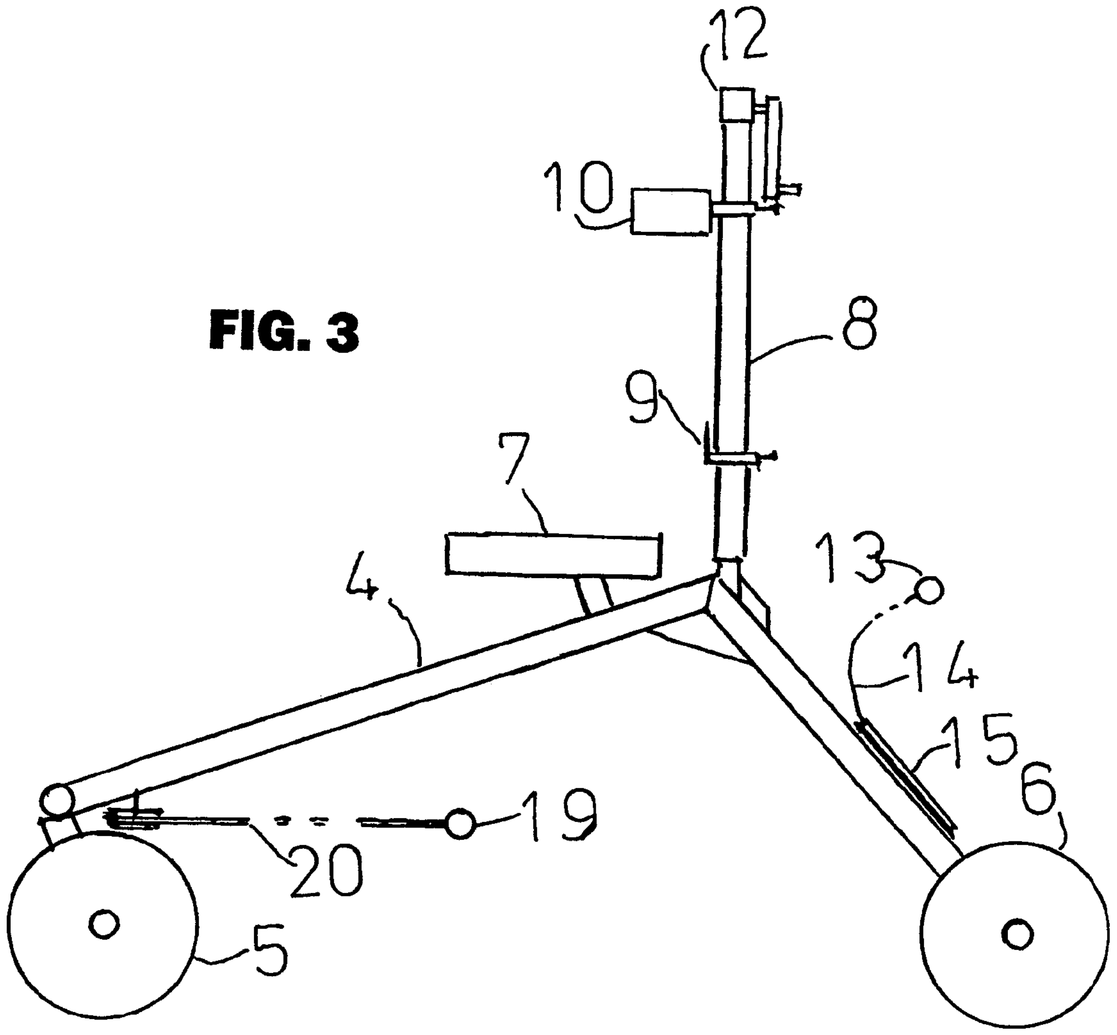
FIG. 3 is a side elevation view of the walker of the invention.

A knee engagement means 13 engages the brace at each knee or the knee itself. Each knee engagement means 13 is connected by a cord 14 to a control mechanism 15 mounted on the frame behind the vertical member 8. The mechanism 15, as best seen in FIGS. 6 and 7, includes a plate 31 pivoted at pivot 32 on the frame 1. Each cord 14 is attached at an attachment 34 to the plate. In FIG. 6 both knees are equidistant from mechanism 15 as the patient is standing. The mechanism 15 prevents both knees from moving forward together. When the patient walks by advancing the right knee, as in FIG. 7, plate 31 is rotated counterclockwise by tension on the right cord 14. The frame is pulled forward, and slack in the left cord is taken up as it wraps around cylinder 33 at pivot 32. Action is reversed when the next step is taken. This mechanism encourages a normal gait with restraining normal motions.

A shoe cord 20 has a shoe engaging element 19 at each end that may be fastened to each shoe 18, or to the brace at the shoe level. A bight 21 is slidingly supported by pulley 22 mounted on the frame forward of the patient. The shoe cord length is adjusted so as to prevent simultaneous rearward motion of both feet, while enabling forward motion of one shoe at a time in normal gait. A pair of elastic cords 23 each have a first end 26 attached to the frame. A guide 24 is attached to each cord second end 27. The guide permits the cord 23 to pass therethrough. However it is too small to permit the stop 25 to pass therethrough. When a shoe is at its greatest distance from the front of the frame, the stop pulls on the guide and stretches the elastic cord. This occurs when the patient is about to step forward with that shoe. The stretched elastic cord 23 pulls that shoe forward, thereby assisting in the walking process.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. A walking support apparatus for a person wearing a body brace, the body brace including a torso-encircling member and articulated leg braces depending therefrom, the apparatus comprising:
a) a rigid frame;
b) at least one front wheel mounted on the frame;
c) at least one rear wheel mounted on the frame;
d) a seat removably mounted on the frame above the level of the wheels;
e) a vertical support member extending upward from the frame behind the seat and before the rear wheels;
f) engagement means for removably engaging a rear portion of the torso encircling member, the engagement means connected to the vertical support member;
g) a chest engaging member connected to the vertical support member above the engagement means;
h) means for adjusting the distance between the connection of the chest engaging member to the vertical support member and the engagement means to fit a particular person; and
i) the vertical support member provided with vertical adjustment means for adjusting the elevation of the vertical support member above the frame so as to lift a seated person to a standing and walking position after the brace and chest engaging member have connected the person to the vertical support member.

2. The apparatus according to claim 1 further comprising:
a) a knee engagement means for engaging each leg of the person at the knee;
b) a cord connecting each knee engagement means to a control mechanism on the frame behind the the person; and
c) said control mechanism constructed so as to enable forward motion of one knee at a time while taking up slack in the cord to the other knee.

3. The apparatus according to claim 2 further comprising:
a) a shoe engaging element on each of two shoes;
b) a shoe cord having a connector at each end connected to one of the shoe engaging elements;
c) a bight of the shoe cord slidingly supported by the frame forward of the person; and
d) the shoe cord length adjusted to prevent simultaneous rearward motion of the shoes, while enabling forward motion of one shoe at a time to thereby enhance walking.

4. The apparatus according to claim 1 further comprising:
a) a shoe engaging element on each of two shoes;
b) a shoe cord having a connector at each end connected to one of the shoe engaging elements;
c) a bight of the shoe cord slidingly supported by the frame forward of the person; and
d) the shoe cord length adjusted to prevent simultaneous rearward motion of the shoes, while enabling forward motion of one shoe at a time to thereby enhance walking.

5. The apparatus according to claim 4 further comprising:
a) a pair of elastic cords, each elastic cord attached at a first end to a forward portion of the frame;
b) a guide at a second end of each elastic cord, the guide freely passing a portion of the shoe cord adjacent an end therethrough; and
c) a stop at the bight of the shoe cord dimensioned to stop the shoe cord from further passage through the guide to thereby apply forward bias to the shoe when it is at its greatest distance from the forward end of the frame.

6. A walking therapy apparatus for a person, the apparatus comprising:
a) a rigid frame;
b) at least one front wheel mounted on the frame;
c) at least one rear wheel mounted on the frame;
d) a knee engagement means for engaging each leg of the person at the knee;
e) a cord connecting each knee engagement means to a control mechanism on the frame behind the person; and
f) the control mechanism constructed so as to enable forward motion of one knee at a time while taking up slack in the cord to the other knee.

7. The apparatus according to claim 6 further comprising:
a) a shoe engaging element on each of two shoes;
b) a shoe cord having a connector at each end connected to one of the shoe engaging elements;
c) a bight of the shoe cord slidingly supported by the frame forward of the person; and
d) the shoe cord length adjusted to prevent simultaneous rearward motion of the shoes, while enabling forward motion of one shoe at a time to thereby enhance walking.

8. The apparatus according to claim 7 further comprising:
a) a pair of elastic cords, each elastic cord attached at a first end to a forward portion of the frame;
b) a guide at a second end of each elastic cord, the guide freely passing a portion of the shoe cord adjacent an end therethrough; and
c) a stop at the bight of the shoe cord dimensioned to stop the shoe cord from further passage through the guide to thereby apply forward bias to the shoe when it is at its greatest distance from the forward end of the frame.

9. A walking support apparatus for a person wearing a body brace, the body brace including a torso-encircling member and articulated leg braces depending therefrom, the apparatus comprising:
a) a rigid frame;
b) at least one front wheel mounted on the frame;
c) at least one rear wheel mounted on the frame;
d) a vertical support member extending upward from the frame before the rear wheels;

e) engagement means for removably engaging a rear portion of said body brace including a torso encircling member and articulated leg braces depending therefrom, the engagement means connected to the vertical support member;

f) a chest engaging member connected to the vertical support member above the engagement means; and g) means for adjusting the distance between the connection of the chest engaging member to the vertical support member and the engagement means to fit a particular person.

10. The apparatus according to claim 9 further comprising:

a) a knee engagement means for engaging each leg of the person at the knee;

b) a cord connecting each knee engagement means to a control mechanism on the frame behind the the person; and c) said control mechanism constructed so as to enable forward motion of one knee at a time while taking up slack in the cord to the other knee.

11. The apparatus according to claim 10 further comprising:

a) a shoe engaging element connecting a shoe to each leg brace at a lower end thereof b) a shoe cord having a connector at each end connected to one of the shoe engaging elements;

c) a bight of the shoe cord slidingly supported by the frame forward of the person; and d) the shoe cord length adjusted to prevent simultaneous rearward motion of the shoes, while enabling forward motion of one shoe at a time to thereby enhance walking.

12. The apparatus according to claim 11 further comprising:

a) a pair of elastic cords, each elastic cord attached at a first end to a forward portion of the frame;

b) a guide at a second end of each elastic cord, the guide freely passing a portion of the shoe cord adjacent an end therethrough; and c) a stop at the bight of the shoe cord dimensioned to stop the shoe cord from further passage through the guide to thereby apply forward bias to the shoe when it is at its greatest distance from the forward end of the frame.

13. The apparatus according to claim 9 further comprising:

a shoe engaging element on each of two shoes;

a shoe cord having a connector at each end connected to one of the shoe engaging elements;

a bight of the shoe cord slidingly supported by the frame forward of the person; and the shoe cord length adjusted to prevent simultaneous rearward motion of the shoes, while enabling forward motion of one shoe at a time to thereby enhance walking.

14. The apparatus according to claim 13 further comprising:

a) a pair of elastic cords, each elastic cord attached at a first end to a forward portion of the frame;

b) a guide at a second end of each elastic cord, the guide freely passing a portion of the shoe cord adjacent an end therethrough; and c) a stop at the bight of the shoe cord dimensioned to stop the shoe cord from further passage through the guide to thereby apply forward bias to the shoe when it is at its greatest distance from the forward end of the frame.

15. A walking support apparatus for a person wearing a body brace, the body brace including a torso-encircling member and articulated leg braces depending therefrom, the apparatus comprising:

a) a rigid frame;

b) at least one front wheel mounted on the frame;

c) at least one rear wheel mounted on the frame;

d) a vertical support member extending upward from the frame between the front and the rear wheels;

e) engagement means for removably engaging a rear portion of said body brace including a torso encircling member and articulated leg braces depending therefrom, the engagement means connected to the vertical support member;

f) a chest engaging member connected to the vertical support member above the engagement means;

g) means for adjusting the distance between the connection of the chest engaging member to the vertical support member and the engagement means to fit a particular person; and h) the vertical support member provided with vertical adjustment means for adjusting the elevation above the frame so as to support the person at a comfortable standing and walking position after the brace and chest encircling member have connected the person to the vertical support member.

16. The apparatus according to claim 3 further comprising:

a) a pair of elastic cords, each elastic cord attached at a first end to a forward portion of the frame;

b) a guide at a second end of each elastic cord, the guide freely passing a portion of the shoe cord adjacent an end therethrough; and c) a stop at the bight of the shoe cord dimensioned to stop the shoe cord from further passage through the guide to thereby apply forward bias to the shoe when it is at its greatest distance from the forward end of the frame.

* * * * *